United States Patent [19]

Perrin

[11] Patent Number: 5,332,749
[45] Date of Patent: Jul. 26, 1994

[54] QUINOLONES, PROCESS FOR THEIR PREPARATION AND PHARMACEUTICAL COMPOSITIONS CONTAINING SAME

[75] Inventor: Claude Perrin, Orsay, France
[73] Assignee: Bouchara, France
[21] Appl. No.: 946,315
[22] PCT Filed: Feb. 27, 1992
[86] PCT No.: PCT/FR92/00177
  § 371 Date: Oct. 30, 1992
  § 102(e) Date: Oct. 30, 1992
[87] PCT Pub. No.: WO92/15574
  PCT Pub. Date: Sep. 17, 1992

[30] Foreign Application Priority Data

Mar. 1, 1991 [FR] France .................. 91 02585

[51] Int. Cl.⁵ .............. A61K 31/47; C07D 215/16
[52] U.S. Cl. .................. 514/312; 514/314; 546/156
[58] Field of Search .............. 546/156; 514/312, 314

[56] References Cited

U.S. PATENT DOCUMENTS 4,851,418  7/1989  Sanchez .................. 546/156
4,894,458  1/1990  Masuzawa et al. .......... 546/156

Primary Examiner—C. Warren Ivy
Assistant Examiner—Raymond Covington
Attorney, Agent, or Firm—Bierman and Muserlian

[57] ABSTRACT

The invention concerns organic chemistry and, more precisely, therapeutic chemistry. It describes specifically novel 6-fluoro 7-piperdinyl quinolone-3 carboxylic acids having general formula (I)

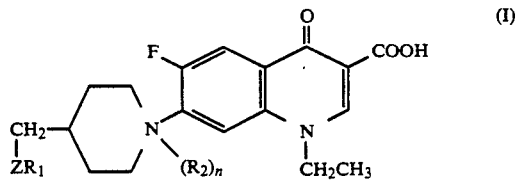

in which Z is an amino radical, and R1 is a radical (lower optionally hydroxylated alkyl), an acyl radical derived from a carboxylic organic acid, from an alkyl carbonic acid, or from an alkylsulfonic acid, or a carbonyl arylamino radical having formula (II)

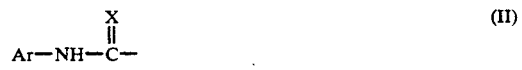

in which Ar is a mono or bicyclic aromatic radical, optionally substituted by one, two or three substituents selected form lower alkyls, halogens and trifluoromethyl; and X is oxygen or sulphur. The invention also concerns the addition salts of said acids. The compounds of general formula (I) constitute the active ingredients of antibacterial drugs.

5 Claims, No Drawings

QUINOLONES, PROCESS FOR THEIR PREPARATION AND PHARMACEUTICAL COMPOSITIONS CONTAINING SAME

The present invention relates to novel quinolones and more particularly to quinolones substituted with a piperidinyl ring.

More particularly it has a subject matter novel piperidinyl quinolone 3-carboxylic acids having the general formula I $$\text{(I)}$$

wherein Z represents an amino group and $R_1$ represents a lower alkyl radical which may be substituted with a hydroxy, an acyl residue coming from a carboxylic organic acid, an alkylcarbonic acid, an alkyl sulphonic acid or an arylamino carbonyl group of the formula $$Ar-NH-\overset{X}{\underset{\|}{C}}-X$$

wherein Ar is an aromatic mono- or bicyclic radical which is optionally substituted by one, two or three substituents selected from the group consisting of a lower alkyl radical, a halogen, and a trifluoromethyl X represents oxygen or sulphur $R_2$ is an oxygen bound to the nitrogen by a semi polar valency and n is equal to 0 or 1

Among the compounds of this invention, it may distinguished three sub-groups.

a) The amino and alkylamino derivatives of formula $I_A$ $$\text{(}I_A\text{)}$$

wherein $R_1$ represents hydrogen or a lower alkyl radical, which is straight or branched and which may be substituted by a hydroxy.

b) The acylamino derivatives of formula $I_B$ $$\text{(}I_B\text{)}$$

wherein Ac represents the residue of an aliphatic, aromatic or cyclanic carboxylic acid having from 1 to 10 carbon atoms, the residue of an alkylcarbonic acid or the residue of an alkyl sulphonic acid which may be substituted with a hydroxy or a trifluoromethyl radical.

The (uriedo) derivatives of formula $I_c$ $$\text{(}I_c\text{)}$$

wherein X represents oxygen or sulphur
W is a group $\geq$CH or $\geq$N
B is hydrogen or a ring structure having 5 or 6 links
Z is hydrogen, a lower alkyl radical a trifluoromethyl radical or a halogen
and p is equal to 1, 2 or 3

Amoug the compounds of general formula I, the compounds for which Z, $R_1$ is an ureido group are those which are presently preferred.

The compounds according to this invention may be salified by adding a mineral or organic base. The main salts which are useful, are those of alkali-metals, of alkaline metals, of iron, of ammonium, the alkylamine salts, the hydroxy alkyl amine salts, the phenylalkylamine salts, the pyridylalkylamine salts, the cyclanylamine salts, the dicyclanylamine salts.

Among these salts, the salts of sodium, lithium, ammonium, N-methyl glucamine and tromethanol are those presently preferred.

These compounds may also exist in the form of a N-oxide the solubility in water and in the biological media of which is improved.

These compounds may also be salified by a strong mineral or organic acid when $R_1$ is hydrogen, a lower alkyl radical or a lower hydroxyalkyl radical.

The compounds according to the invention show very strong antibacterial properties, namely against Gram positive bacterias.

Moreover they have the properties to be very slightly resorbed through the digestive tract and consequently their elimination is essentially fecal.

They may be then efficiently be used as medicines of the bacterial infections of the digestive tract, for treating bacterial dysentery traveller's diarrhea, or intestinal infections. They may also be utilized topically for the treatment of the ocular infections or in conjunction the infections of the auditive tract.

For these purposes the compounds according to this invention are utilized in the form of pharmaceutical compositions wherein the active ingredient of general formula I or one of its salts is admixed with a carrier or vehicle, which is inert, non-toxic, pharmaceutical-acceptable.

The more appropriate pharmaceutical forms are those intended for the administration through the digestive tract such as the drinkable suspensions or solutions, the granules, the capsules, the uncoated or coated tablets, the dragees, the sachets of powders, which may be flavoured or not, sweetened or not, the pills or the cachets.

For the topic application as an external antibacterial-agent, they may be used in the form of solutions, creames, salves, and gels.

The daily dosage mainly depends on the severity of the infection and on the susceptibility of the microbial strain to the antibacterial-agent. The unitary dosology ranges from 100 to 600 mg per unit dosage. The daily dose ranges from 200 to 1200 mg divided in two intakes.

This invention also relates to a process for obtaining the compounds of general formula I in which 6-fluoro 7-chloro 1-ethyl 4-oxo 1,4-dihydroquinoleinyl-3 carboxylic acid of formula II

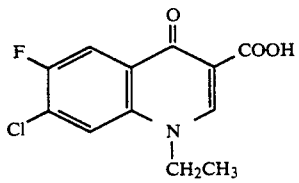
(II)

is reacted with 4-(aminomethyl) piperidine in basic medium to produce a 6-fluoro 7-(4-aminomethyl piperidinyl-1) 4-oxo 1,4-dihydroquinoleinyl-3 carboxylic acid of formula III

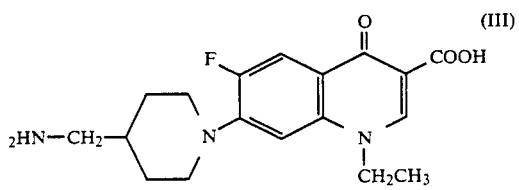
(III)

which may, when desired, be
- salified by adding a mineral or organic base
- converted into an addition salt by adding a mineral or organic acid
- transformed into a N-oxide by action of a mineral or organic hydroperoxide
- alkylated by means of an alkyl halide in basic medium or acylated by reaction with a functional derivative of a carboxylic or sulphonic acid or with an alkyl halogeno formate.

This invention further relates to a process for converting an amidated derivative of formula III into an Urea or a Thio Urea, which consists in submitting a compound of formula III to the action of an aryl isocyanate or isothiocyanate having the formula

Ar—N=C=X wherein Ar and X have the previously given definitions as a solution in an inert solvent, to produce the ureido derivative of formula IV

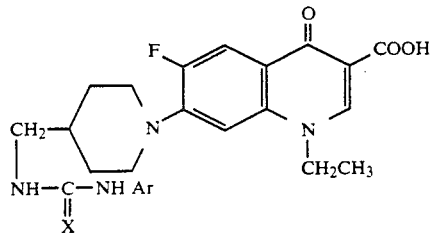
(IV)

wherein X and Ar are defined as previously.

The following examples are merely intended to illustrate the invention without limiting it.

EXAMPLE I

6-FLUORO 7-(4-AMINOMETHYL PIPERIDINYL-1) 1-ETHYL 4-OXO 1,4-DIHYDRO QUINOLEVINYL-3 CARBOXYLIC ACID

A solution of 5,39 g (0,02M) of 6-fluoro 7-chloro 1-ethyl 4-oxo 1,4-dihydroquinoleinyl 3-carboxylic acid and of 3.71 g (0,03M) of 4-aminomethyl piperidine in 50 ml of pyridine is heated for 24 h at reflux. After this period, the thus formed crystals are separated, they are perfectly dried and the recovered mixture is conveniently crystallized in a mixture of dimethyl formamide-ethanol.

There are thus recovered 4,25 g of pale yellow crystals, melting (Koffler block) at 190° C. IR spectrum and elementar analysis are in accordance with a crystallized product with 1,5 mol water.

After recrystallization from dimethyl formamide, 3,65 g of pale yellow crystals are recovered (yield 52%) which melts at 192° C.

IR spectrum: CO at 3400 cm$^{-1}$

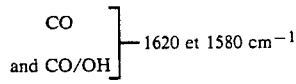

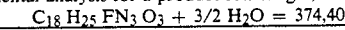

| Elemental analysis for a product retaining 1,5 mol water: $C_{18} H_{25} FN_3 O_3 + 3/2 H_2O = 374,40$ | | | | | |
|---|---|---|---|---|---|
| | C | H | F | N | O % |
| Calculated | 57.74 | 7.73 | 5.07 | 11.22 | 19.2.. |
| Found | 57.16 | 6.63 | 5.02 | 11.22 | |
| | 57.45 | 6.81 | | | |

EXAMPLE II

7-[4-(PHENYLAMINOCARBONYLAMINOMETHYL)PIPERIDINYL-1] 6-FLUORO 1-ETHYL 4-OXO 1,4-DIHYDROQUINOLEINYL-3 CARBOXYLIC ACID 3.47 g (0,01M) of 7-(4-aminomethyl piperidinyl-1) 6-fluoro 1-ethyl 4-oxo 1,4-dihydroquinoleinyl-3 carboxylic acid are dissolved into 30 ml of dimethyl formamide. The solution is added quickly, under stirring to 3 ml of phenyl isocyanate i.e. 3,28 g.

The mixture is then heated to 120° C. for 3 hours, and kept aside for a night.

The thus formed crystals are separated, the they are recrystallized from methylformamide then they are washed with ethanol. 2,07 g of colourless crystals are thus recovered (yield 45%) melting above 260° C.

| IR Spectrum: | |
|---|---|
| CO at 1735 cm$^-$ | |
| CO of the —NH— and carbonyl | 1630 cm$^{-1}$ |

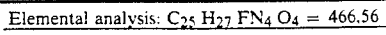

| Elemental analysis: $C_{25} H_{27} FN_4 O_4 = 466.56$ | | | | |
|---|---|---|---|---|
| | C | H | F | N | O % |
| Theoretical | 64.36 | 5.83 | 4.07 | 12.01 | 13.7 |

-continued

Elemental analysis: $C_{25}H_{27}FN_4O_4 = 466,56$

|  | C | H | F | N | O % |
|---|---|---|---|---|---|
| Found | 64.16 | 5.77 | 4.22 | 11.88 |  |
|  | 64.26 | 5.87 |  |  |  | similarly they have been produced

| p.methylphenylurea | MP = 247° |
|---|---|
| m.fluorophenylurea | MP = 258° |
| (3,4-dichlorophenyl)Urea | MP = 255° |
| (p.ethoxycarbonylphenyl)Urea | MP = 239° |
| (p.methoxyphenyl)Urea | MP = 241° |
| (p.nitrophenyl)Urea | MP = 254° |
| (2,4-difluorophenyl)Urea | MP = 241° |
| (2-fluorophenyl)Urea | MP = 235° |
| (Naphtyl-1)Thiourea | MP = 260° |
| (Naphtyl-1)Urea | MP = 255° |
| (m-methoxyphenyl)Urea | MP = 244° |
| (3,4-dichlorophenyl)Urea | MP = 258° |

Bacteriological studies of the compounds of this invention:

I) Material and Methods 1. in the first step of screening, the compounds have been tested versus 6 strains of reference i.e. 3 gram positive strains Bacillus substilis ATCC 93 722
Staphylococcus aureus ATCC 25 923
Streptococcus faecalis ATCC 8 043
and 3 Gram- negative strains
Escherichia coli ATCC 25 922
Pseudomonas aeruginosa ATCC 2 285
Acinetobacter calcoaceticus var. anitratum FATCC 17 903.

2. The measure of the minimal inhibiting concentrations (MIC) has been performed using a microdilution method with microplates and in moculator Dynatech, in liquid medium (Mueller-Hinton's broth) under a volume of 100 µl and for a range of concentrations from 128 to 0,06 mg/l prepared starting from a mother liquor titrating 512 mg/l. The preparation of the mother solutions done according to the manufacturer's directions, varied from molecule to molecule.

Inoculation has been performed by adding in each capsule 10 µl of a dilution in sale of a broth of 18 hours old (heart/brain) such as each cupule contained about $10^6$ bacterias/ml.

The mineral inhibitory concentration has been read as the first concentration of antibiotic substance which does not provide any growth, macroscopically apparent after 18 h incubation at 37° C.

RESULTS

The compound of example II has been found the most active. Particularly as regard to Staphylococcus aureus
MIC is 0.2 mcg/ml
MBC is 0.5 mcg/ml
and as regard Escherichia coli
MIC is 8 mcg/ml
MBC is 8 mcg/ml.

What is claimed is:

1. A compound selected from the group consisting of a compound of the formula

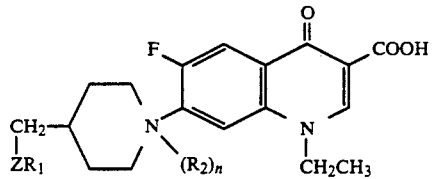

wherein Z is amino, $R_1$ is selected from the group consisting of linear alkyl, hydroxy lower alkyl, acyl of an organic carboxylic acid, alkylcarbonic acid and alkyl sulfonic acid and

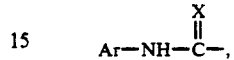

Ar is a mono-or bicyclic aryl optionally substituted with 1 to 3 substituents selected from the group consisting of lower alkyl, halogen and $-CF_3$, $R_2$ is oxygen bound with a semi-polar valency and n is 0 or 1 and their non-toxic, pharmaceutically acceptable salts with a base or an acid when $R_1$ is hydrogen, lower alkyl or hydroxy lower alkyl X is O or S.

2. A compound of claim 1 of the formula

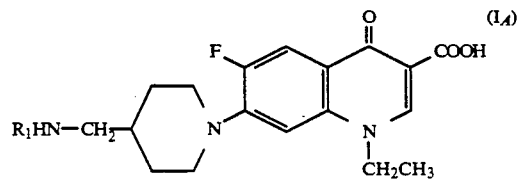

wherein $R_1$ is selected form the group consisting of hydrogen, lower alkyl and hydroxy lower alkyl.

3. A compound of claim 1 of formula

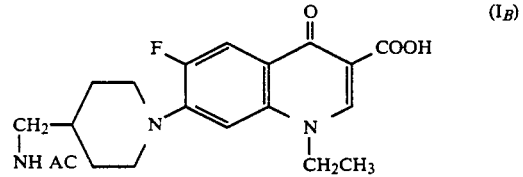

wherein Ac is selected from the group consisting of acyl of an aliphatic, aromatic or cycloalkyl carboxylic acid of up to 10 carbon atoms, acyl of an alkylcarbonic or alkyl sulfonic acid optionally substituted with $-OH$ or $-CF_3$.

4. A compound of claim 1 of the formula

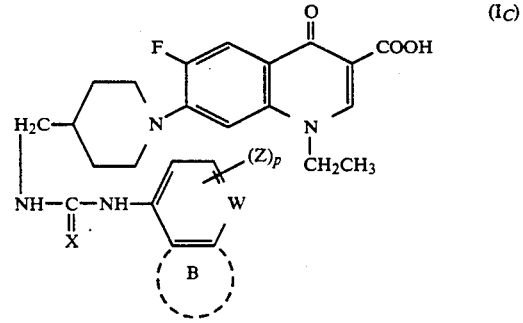

wherein X is =O or =S, B is hydrogen or aryl of 5 to 6 ring members, Z is selected from the group consisting of hydrogen, $-CF_3$, halogen and lower alkyl and p is 1 or 2 or 3 is CH or N.

5. An antibacterial composition comprising an bactericidally effective amount of a compound of claim 1 and a inert pharmaceutical carrier.

* * * * *